(12) United States Patent
Hayasaka et al.

(10) Patent No.: US 7,803,914 B2
(45) Date of Patent: Sep. 28, 2010

(54) METHODS FOR STABILIZING PROTEIN SOLUTIONS

(75) Inventors: Akira Hayasaka, Shizuoka (JP); Tomoyuki Igawa, Shizuoka (JP); Yasuo Sekimori, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 297 days.

(21) Appl. No.: 10/574,827

(22) PCT Filed: Oct. 8, 2004

(86) PCT No.: PCT/JP2004/014919

§ 371 (c)(1),
(2), (4) Date: Mar. 27, 2007

(87) PCT Pub. No.: WO2005/035573

PCT Pub. Date: Apr. 21, 2005

(65) Prior Publication Data

US 2007/0249812 A1    Oct. 25, 2007

(30) Foreign Application Priority Data

Oct. 9, 2003    (JP) .............................. 2003-351410

(51) Int. Cl.
*C07K 16/00*    (2006.01)
(52) U.S. Cl. .................. 530/387.1; 424/130.1
(58) Field of Classification Search .............. 530/387.1; 424/130.1
See application file for complete search history.

(56) References Cited

U.S. PATENT DOCUMENTS

| | | | |
|---|---|---|---|
| 5,157,113 | A | 10/1992 | Dove et al. |
| 5,190,752 | A | 3/1993 | Möller et al. |
| 5,792,838 | A | 8/1998 | Smith et al. |
| 5,908,826 | A | 6/1999 | Fukuda et al. |
| 6,136,312 | A | 10/2000 | Rentsch |
| 6,238,891 | B1 | 5/2001 | Maiorella et al. |
| 2002/0119530 | A1 | 8/2002 | Maiorella et al. |
| 2004/0170623 | A1 | 9/2004 | Tudor et al. |
| 2005/0118167 | A1 | 6/2005 | Akira et al. |
| 2006/0127395 | A1 | 6/2006 | Tudor et al. |
| 2007/0154469 | A1 | 7/2007 | Irie et al. |
| 2007/0212346 | A1 | 9/2007 | Igawa et al. |
| 2009/0285802 | A1 | 11/2009 | Igawa et al. |

FOREIGN PATENT DOCUMENTS

| | | |
|---|---|---|
| EP | 0352500 | 7/1989 |
| EP | 0 492 409 | 7/1992 |
| EP | 0531539 A1 | 3/1993 |
| EP | 1174148 | 1/2002 |
| JP | 2-000493 | 1/1990 |
| JP | 2-078635 | 3/1990 |
| JP | 6-189781 | 7/1994 |
| JP | 7-502497 | 3/1995 |
| JP | 9-127112 | 5/1997 |
| JP | 9-127114 | 5/1997 |
| JP | 2001-504092 | 3/2001 |
| WO | WO 89/01975 | 3/1989 |
| WO | WO 89/04867 | 6/1989 |
| WO | WO 91/18106 | 11/1991 |
| WO | WO 93/08837 | 5/1993 |
| WO | WO 99/37329 | 7/1999 |
| WO | WO 00/66160 | 11/2000 |
| WO | WO 02/096457 | 12/2002 |
| WO | WO 03/046162 | 6/2003 |
| WO | WO 2005/005636 | 1/2005 |
| WO | WO 2005/035574 | 4/2005 |

OTHER PUBLICATIONS

Chen et al., "Strategies to Suppress Aggregation of Recombinant Keratinocyte Growth Factor During Liquid Formulation Development," *J. Pharm. Sci.*, 83:1657-1661 (1994).
Dráber et al., "Stability of Monoclonal IgM Antibodies Freeze-Dried in the Presence of Trehalose," *Journal of Immunological Methods*, 181:37-43 (1995).
García-González et al., "Purification of Murine IgG3 and IgM Monoclonal Antibodies by Euglobulin Precipitation," *Journal of Immunological Methods*, 111:17-23 (1988).
Gombotz et al., "The Stabilization of a Human IgM Monoclonal Antibody with Poly(vinylpyrrolidone)," *Pharm. Res.* 11:624-632 (1994).
Molina et al., "The Effects of Divalent Cations in the Presence of Phosphate, Citrate and Chloride on the Aggregation of Soy Protein Isolate," *Food Research International*, 32:135-143 (1999).
Sharma et al., "Study of IgM Aggregation in Serum of Patients with Macroglobulinemia," *Clin. Chem. Lab. Med.*, 38:759-764 (2000).
Phillips et al., "Manufacture and quality control of CAMPATH-1 antibodies for clinical trials," *Cytotherapy*, 3:233-242 (2001).
Jones et al., "Replacing the complementarity-determining regions in a human antibody with those from a mouse," *Nature*, 321:522-525 (1986).
Kallemuchikkal et al., "Evaluation of cryoglobulins," *Arch. Pathol. Lab. Med.*, 123:119-125 (1999).
Middaugh et al., "Effect of solutes on the cold-induced insolubility of monoclonal cryoimmunoglobulins," *J. Biol. Chem.*, 252:8002-06 (1977).
Middaugh et al., "Molecular basis for the temperature-dependent insolubility of cryoglobulins. IV. Structural studies of the IgM monoclonal cryoglobulin McE," Immunochem., 15:171-187 (1978).
Morrison et al., "Chimeric human antibody molecules: Mouse antigen-binding domains with human constant region domains," *Proc. Natl. Acad. Sci. USA*, 81:6851-55 (1984).
Page et al., "Purification of monoclonal antibodies," *Methods Mol. Biol.*, 80:113-119 (1998).
Steinbuch et al., "Preparation of an IgM and IgA enriched fraction for clinical use," *Prep. Biochem.*, 3:363-373 (1973).
Nifong et al., "Separation of IgG and IgM from albumin in citrated human plasma using electrodialysis and metal ion affinity precipitation," *ASAIO J.*, 48:645-649 (2002).

(Continued)

*Primary Examiner*—Chih-Min Kam
(74) *Attorney, Agent, or Firm*—Fish & Richardson P.C.

(57) ABSTRACT

The present inventors examined use of citric acid buffers for suppressing cryoprecipitation of IgM at a pH range and salt concentration suitable for storing IgM. As a result, the present inventors discovered that citric acid buffers significantly suppress cryoprecipitation.

18 Claims, 4 Drawing Sheets

OTHER PUBLICATIONS

Arya et al., "Mapping of Amino Acid Residues in the Cµ3 Domain of Mouse IgM Important in Macromolecular Assembly and Complement-Dependent Cytolysis," *J. Immunol.*, 152:1206-12 (1994).

Brewer et al., "Mechanism and Subcellular Localization of Secretory IgM Polymer Assembly," *J. Biol. Chem.*, 269:17338-48 (1994).

Cattaneo et al., "Polymeric Immunoglobulin M is Secreted by Transfectants of Non-Lymphoid Cells in the Absence of Immunoglobulin J Chain," *EMBO J.*, 6:2753-58 (1987).

Green, L., "Antibody engineering via genetic engineering of the mouse: XenoMouse strains are a vehicle for the facile generation of therapeutic human monoclonal antibodies," *J Immunol. Methods*, 231:11-23 (1999).

Haruta et al., "Class-Switching of the IgM Type Anit-Adenocarcinoma Human Antibody HB4C5 into an IgG1 Type Resulted in the Loss of the Antigen Binding Ability," *Human Antibodies*, 8:137-145 (1997).

Hoon et al., "Molecular cloning of a human monoclonal antibody reactive to ganglioside GM3 antigen on human cancers," *Cancer Res.*, 53:5244-50 (1993).

Huang et al., "Production of Recombinant Murine-Human Chimeric IgM and IgG Anti-Js$^b$ For Use in the Clinical Laboratory," *Transfusion*, 43:758-764 (2003).

Hughey et al., "Production of IgM Hexamers by Normal and Autoimmune B Cells: Implications for the Physiologic Role of Hexameric IgM," *J. Immunol.*, 161:4091-97 (1998).

Irie et al., "Phase I pilot clinical trial of human IgM monoclonal antibody to ganglioside GM3 in patients with metastatic melanoma," *Cancer Immunol. Immunother.*, 53:110-117 (2004).

Kunert et al., "Characterization of Molecular Features, Antigen-Binding, and In Vitro Properties of IgG and IgM Variants of 4E10, an Anti-HIV Type 1 Neutralizing Monoclonal Antibody," *AIDS Res. Hum. Retroviruses*, 20:755-762 (2004).

Mayus et al., "Inhibition of In Vitro Anti-DNA B-Cell Responses by Cyclosporine," *Cell. Immunol.*, 94:195-204 (1985).

Meng et al., "J Chain Deficiency in Human IgM Monoclonal Antibodies Produced by Epstein-Barr Virus-Transformed B Lymphocytes," *Eur. J. Immunol.*, 20:2505-08 (1990).

Monica et al., "Comparative Biochemical Characterization of a Human IgM Produced in Both Ascites and In Vitro Cell Culture," *Biotechnology*, 4:512-515 (1993).

Niles et al., "Polymer IgM Assembly and Secretion in Lymphoid and Nonlymphoid Cell Lines: Evidence that J Chain is Required for Pentamer IgM Synthesis," *Proc. Natl. Acad. Sci. USA*, 92:2884-88 (1995).

Randall et al., "Direct Evidence That J Chain Regulates the Polymeric Structure of IgM in Antibody-secreting B Cells," *J Biol. Chem.*, 267:18002-07 (1992).

Randall et al., "J Chain Synthesis and Secretion of Hexameric IgM is Differentially Regulated by Lipopolysaccharide and Interleukin 5," *Proc. Natl. Acad. Sci. USA*, 89:962-966 (1992).

Shitara et al., "Immunoglobulin Class Switch of Anti-Ganglioside Monoclonal Antibody from IgM to IgG," *J. Immunol. Methods*, 169:83-92 (1994).

Sorensen et al., "Structural Requirements for Incorporation of J Chain into Human IgM and IgA," *Int. Immunol.*, 12:19-27 (2000).

Stocks et al., "Production and Isolation of Large Quantities of Monoclonal Antibody Using Serum-Free Medium and Fast Protein Liquid Chromatography," *Hybridoma*, 8:241-247 (1989).

Stoll et al., "Effects of culture conditions on the production and quality of monoclonal IgA," *Enzyme Microb. Technol.*, 21:203-211 (1997).

Tachibana, "Gene expression of joining chain in murine peritoneal B-1 cells," *Nihon Univ. Dent. J.*, 76:425-433 (2002) (English abstract included).

Wood et al., "High Level Synthesis of Immunoglobulins in Chinese Hamster Ovary Cells," *J. Immunol.*, 145:3011-16 (1990).

Youd et al., "Synergistic roles of IgM and complement in antigen trapping and follicular localization," *Eur. J. Immunol.*, 32:2328-37 (2002).

USPTO Restriction Requirement in U.S. Appl. No. 10/564,665, dated Jul. 9, 2008, 7 pages.

Fish & Richardson P.C., Response to Restriction Requirement dated Jul. 9, 2008, in U.S. Appl. No. 10/564,665, filed Aug. 8, 2008, 1 page.

USPTO Restriction Requirement in U.S. Appl. No. 10/564,665, dated Nov. 12, 2008, 6 pages.

Fish & Richardson P.C., Response to Restriction Requirement dated Nov. 12, 2008, in U.S. Appl. No. 10/564,665, filed Jan. 9, 2009, 1 page.

USPTO Non-Final Office Action in U.S. Appl. No. 10/564,665, dated Apr. 20, 2009, 16 pages.

Japanese Patent Office, International Search Report for App. Ser. No. PCT/JP2004/010444, mailed Oct. 26, 2004, 4 pages.

Fish & Richardson P.C. Amendment in Reply to Action dated Apr. 20, 2009 in U.S. Appl. No. 10/564,665, filed Oct. 19, 2009, 6 pages.

USPTO Notice of Allowance in U.S. Appl. No. 10/564,665, dated Dec. 4, 2009, 11 pages.

European Search Report for App. Ser. No. EP 04 79 2188, dated Sep. 21, 2009, 4 pages.

Japanese Patent Office, International Preliminary Report on Patentability for App. Ser. No. PCT/JP2004/010444, dated Jun. 3, 2005, 5 pages.

Japanese Patent Office, International Search Report for App. Ser. No. PCT/JP2004/014919, mailed Dec. 7, 2004, 4 pages.

Japanese Patent Office, International Preliminary Report on Patentability for App. Ser. No. PCT/JP2004/014919, dated Sep. 12, 2005, 14 pages.

USPTO Restriction Requirement in U.S. Appl. No. 10/575,192, dated Apr. 15, 2008, 7 pages.

Fish & Richardson P.C., Response to Restriction Requirement dated Apr. 15, 2008 in U.S. Appl. No. 10/575,192, filed Sep. 12, 2008, 1 page.

USPTO Non-Final Office Action in U.S. Appl. No. 10/575,192, dated Jan. 26, 2009, 11 pages.

Japanese Patent Office, International Search Report for App. Ser. No. PCT/JP2004/014935, mailed Jan. 25, 2005, 4 pages.

Japanese Patent Office, International Preliminary Report on Patentability for App. Ser. No. PCT/JP2004/014935, 14 pages, (Sep. 2005).

European Search Report for App. Ser. No. Ep 04 79 2204, mailed Jul. 11, 2007, 3 pages.

| | | | | |
|---|---|---|---|---|
| 8 mg/ml |  | A1<br>STABLE |  | C1<br>STABLE |
| 17 mg/ml |  | A2<br>STABLE |  | C2<br>STABLE |
| 25 mg/ml |  | A3<br>STABLE |  | C3<br>STABLE |
| 33 mg/ml |  | A4<br><u>PRECIPITATION</u> |  | C4<br>STABLE |
| 50 mg/ml |  | A5<br><u>PRECIPITATION</u> |  | C5<br>STABLE |

SEQUENCE LISTING

<160> NUMBER OF SEQ ID NOS: 18

<210> SEQ ID NO 1
<211> LENGTH: 1779
<212> TYPE: DNA
<213> ORGANISM: Homo sapiens
<220> FEATURE:
<221> NAME/KEY: CDS
<222> LOCATION: (1)..(1779)
<223> OTHER INFORMATION:

<400> SEQUENCE: 1

```
atg gag ttt ggg ctg agc tgg ctt ttt ctt gtg gct att tta aaa ggt      48
Met Glu Phe Gly Leu Ser Trp Leu Phe Leu Val Ala Ile Leu Lys Gly
1               5                   10                  15
```

-continued

| | | |
|---|---|---|
| gtc cag tgt gag gtg cag ctg ttg gat tct ggg gga ggc ttg gta cag<br>Val Gln Cys Glu Val Gln Leu Leu Asp Ser Gly Gly Gly Leu Val Gln<br>20  25  30 | | 96 |
| cct ggg ggg tgc ctg aga ctc tcc tgt gca gcc tct gga ttc acc ttt<br>Pro Gly Gly Cys Leu Arg Leu Ser Cys Ala Ala Ser Gly Phe Thr Phe<br>35  40  45 | | 144 |
| agc agc tgt gcc atg agc tgg gtc cgc cag gct cca ggg aag ggg ctg<br>Ser Ser Cys Ala Met Ser Trp Val Arg Gln Ala Pro Gly Lys Gly Leu<br>50  55  60 | | 192 |
| gag tgg gtc tca gct att agt ggt agt ggt ggt agc aca tac tac gca<br>Glu Trp Val Ser Ala Ile Ser Gly Ser Gly Gly Ser Thr Tyr Tyr Ala<br>65  70  75  80 | | 240 |
| gac tcc gtg aag ggc cgg ttc acc atc tcc aga gac aaa tcc aag aac<br>Asp Ser Val Lys Gly Arg Phe Thr Ile Ser Arg Asp Lys Ser Lys Asn<br>85  90  95 | | 288 |
| acg ttg tat ctg caa atg aac agc ctg aga gcc gag gac acg gcc gta<br>Thr Leu Tyr Leu Gln Met Asn Ser Leu Arg Ala Glu Asp Thr Ala Val<br>100  105  110 | | 336 |
| tat tac tgt gcg aaa ggt ggc aac gat att ttg act ggt tat tat gct<br>Tyr Tyr Cys Ala Lys Gly Gly Asn Asp Ile Leu Thr Gly Tyr Tyr Ala<br>115  120  125 | | 384 |
| tgg ggc cag gga acc ctg gtc acc gtc tcc tca ggg agt gca tcc gcc<br>Trp Gly Gln Gly Thr Leu Val Thr Val Ser Ser Gly Ser Ala Ser Ala<br>130  135  140 | | 432 |
| cca acc ctt ttc ccc ctc gtc tcc tgt gag aat tcc ccg tcg gat acg<br>Pro Thr Leu Phe Pro Leu Val Ser Cys Glu Asn Ser Pro Ser Asp Thr<br>145  150  155  160 | | 480 |
| agc agc gtg gcc gtt ggc tgc ctc gca cag gac ttc ctt ccc gac tcc<br>Ser Ser Val Ala Val Gly Cys Leu Ala Gln Asp Phe Leu Pro Asp Ser<br>165  170  175 | | 528 |
| atc act ttc tcc tgg aaa tac aag aac aac tct gac atc agc agc acc<br>Ile Thr Phe Ser Trp Lys Tyr Lys Asn Asn Ser Asp Ile Ser Ser Thr<br>180  185  190 | | 576 |
| cgg ggc ttc cca tca gtc ctg aga ggg ggc aag tac gca gcc acc tca<br>Arg Gly Phe Pro Ser Val Leu Arg Gly Gly Lys Tyr Ala Ala Thr Ser<br>195  200  205 | | 624 |
| cag gtg ctg ctg cct tcc aag gac gtc atg cag ggc aca gac gaa cac<br>Gln Val Leu Leu Pro Ser Lys Asp Val Met Gln Gly Thr Asp Glu His<br>210  215  220 | | 672 |
| gtg gtg tgc aaa gtc cag cac ccc aac ggc aac aaa gaa aag aac gtg<br>Val Val Cys Lys Val Gln His Pro Asn Gly Asn Lys Glu Lys Asn Val<br>225  230  235  240 | | 720 |
| cct ctt cca gtg att gct gag ctg cct ccc aaa gtg agc gtc ttc gtc<br>Pro Leu Pro Val Ile Ala Glu Leu Pro Pro Lys Val Ser Val Phe Val<br>245  250  255 | | 768 |
| cca ccc cgc gac ggc ttc ttc ggc aac ccc cgc aag tcc aag ctc atc<br>Pro Pro Arg Asp Gly Phe Phe Gly Asn Pro Arg Lys Ser Lys Leu Ile<br>260  265  270 | | 816 |
| tgc cag gcc acg ggt ttc agt ccc cgg cag att cag gtg tcc tgg ctg<br>Cys Gln Ala Thr Gly Phe Ser Pro Arg Gln Ile Gln Val Ser Trp Leu<br>275  280  285 | | 864 |
| cgc gag ggg aag cag gtg ggg tct ggc gtc acc acg gac cag gtg cag<br>Arg Glu Gly Lys Gln Val Gly Ser Gly Val Thr Thr Asp Gln Val Gln<br>290  295  300 | | 912 |
| gct gag gcc aaa gag tct ggg ccc acg acc tac aag gtg acc agc aca<br>Ala Glu Ala Lys Glu Ser Gly Pro Thr Thr Tyr Lys Val Thr Ser Thr<br>305  310  315  320 | | 960 |
| ctg acc atc aaa gag agc gac tgg ctc ggc cag agc atg ttc acc tgc<br>Leu Thr Ile Lys Glu Ser Asp Trp Leu Gly Gln Ser Met Phe Thr Cys<br>325  330  335 | | 1008 |

```
cgc gtg gat cac agg ggc ctg acc ttc cag cag aat gcg tcc tcc atg    1056
Arg Val Asp His Arg Gly Leu Thr Phe Gln Gln Asn Ala Ser Ser Met
        340                 345                 350 tgt gtc ccc gat caa gac aca gcc atc cgg gtc ttc gcc atc ccc cca    1104
Cys Val Pro Asp Gln Asp Thr Ala Ile Arg Val Phe Ala Ile Pro Pro
            355                 360                 365 tcc ttt gcc agc atc ttc ctc acc aag tcc acc aag ttg acc tgc ctg    1152
Ser Phe Ala Ser Ile Phe Leu Thr Lys Ser Thr Lys Leu Thr Cys Leu
    370                 375                 380 gtc aca gac ctg acc acc tat gac agc gtg acc atc tcc tgg acc cgc    1200
Val Thr Asp Leu Thr Thr Tyr Asp Ser Val Thr Ile Ser Trp Thr Arg
385                 390                 395                 400 cag aat ggc gaa gct gtg aaa acc cac acc aac atc tcc gag agc cac    1248
Gln Asn Gly Glu Ala Val Lys Thr His Thr Asn Ile Ser Glu Ser His
                405                 410                 415 ccc aat gcc act ttc agc gcc gtg ggt gag gcc agc atc tgc gag gat    1296
Pro Asn Ala Thr Phe Ser Ala Val Gly Glu Ala Ser Ile Cys Glu Asp
            420                 425                 430 gac tgg aat tcc ggg gag agg ttc acg tgc acc gtg acc cac aca gac    1344
Asp Trp Asn Ser Gly Glu Arg Phe Thr Cys Thr Val Thr His Thr Asp
    435                 440                 445 ctg ccc tcg cca ctg aag cag acc atc tcc cgg ccc aag ggg gtg gcc    1392
Leu Pro Ser Pro Leu Lys Gln Thr Ile Ser Arg Pro Lys Gly Val Ala
450                 455                 460 ctg cac agg ccc gat gtc tac ttg cta cca cca gcc cgg gag cag ctg    1440
Leu His Arg Pro Asp Val Tyr Leu Leu Pro Pro Ala Arg Glu Gln Leu
465                 470                 475                 480 aac ctg cgg gag tcg gcc acc atc acg tgc ctg gtg acg ggc ttc tct    1488
Asn Leu Arg Glu Ser Ala Thr Ile Thr Cys Leu Val Thr Gly Phe Ser
                485                 490                 495 ccc gcg gac gtc ttc gtg cag tgg atg cag agg ggg cag ccc ttg tcc    1536
Pro Ala Asp Val Phe Val Gln Trp Met Gln Arg Gly Gln Pro Leu Ser
            500                 505                 510 ccg gag aag tat gtg acc agc gcc cca atg cct gag ccc cag gcc cca    1584
Pro Glu Lys Tyr Val Thr Ser Ala Pro Met Pro Glu Pro Gln Ala Pro
    515                 520                 525 ggc cgg tac ttc gcc cac agc atc ctg acc gtg tcc gaa gag gaa tgg    1632
Gly Arg Tyr Phe Ala His Ser Ile Leu Thr Val Ser Glu Glu Glu Trp
530                 535                 540 aac acg ggg gag acc tac acc tgc gtg gtg gcc cat gag gcc ctg ccc    1680
Asn Thr Gly Glu Thr Tyr Thr Cys Val Val Ala His Glu Ala Leu Pro
545                 550                 555                 560 aac agg gtc acc gag agg acc gtg gac aag tcc acc ggt aaa ccc acc    1728
Asn Arg Val Thr Glu Arg Thr Val Asp Lys Ser Thr Gly Lys Pro Thr
                565                 570                 575 ctg tac aac gtg tcc ctg gtc atg tcc gac aca gct ggc acc tgc tac    1776
Leu Tyr Asn Val Ser Leu Val Met Ser Asp Thr Ala Gly Thr Cys Tyr
            580                 585                 590 tga                                                                1779

<210> SEQ ID NO 2
<211> LENGTH: 592
<212> TYPE: PRT
<213> ORGANISM: Homo sapiens

<400> SEQUENCE: 2

Met Glu Phe Gly Leu Ser Trp Leu Phe Leu Val Ala Ile Leu Lys Gly
1               5                   10                  15
```

-continued

```
Val Gln Cys Glu Val Gln Leu Leu Asp Ser Gly Gly Leu Val Gln
             20                  25                  30

Pro Gly Gly Cys Leu Arg Leu Ser Cys Ala Ala Ser Gly Phe Thr Phe
         35                  40                  45

Ser Ser Cys Ala Met Ser Trp Val Arg Gln Ala Pro Gly Lys Gly Leu
 50                  55                  60

Glu Trp Val Ser Ala Ile Ser Gly Ser Gly Ser Thr Tyr Tyr Ala
 65                  70                  75                  80

Asp Ser Val Lys Gly Arg Phe Thr Ile Ser Arg Asp Lys Ser Lys Asn
             85                  90                  95

Thr Leu Tyr Leu Gln Met Asn Ser Leu Arg Ala Glu Asp Thr Ala Val
             100                 105                 110

Tyr Tyr Cys Ala Lys Gly Gly Asn Asp Ile Leu Thr Gly Tyr Tyr Ala
         115                 120                 125

Trp Gly Gln Gly Thr Leu Val Thr Val Ser Ser Gly Ser Ala Ser Ala
     130                 135                 140

Pro Thr Leu Phe Pro Leu Val Ser Cys Glu Asn Ser Pro Ser Asp Thr
145                 150                 155                 160

Ser Ser Val Ala Val Gly Cys Leu Ala Gln Asp Phe Leu Pro Asp Ser
             165                 170                 175

Ile Thr Phe Ser Trp Lys Tyr Lys Asn Asn Ser Asp Ile Ser Ser Thr
             180                 185                 190

Arg Gly Phe Pro Ser Val Leu Arg Gly Gly Lys Tyr Ala Ala Thr Ser
         195                 200                 205

Gln Val Leu Leu Pro Ser Lys Asp Val Met Gln Gly Thr Asp Glu His
     210                 215                 220

Val Val Cys Lys Val Gln His Pro Asn Gly Asn Lys Glu Lys Asn Val
225                 230                 235                 240

Pro Leu Pro Val Ile Ala Glu Leu Pro Pro Lys Val Ser Val Phe Val
             245                 250                 255

Pro Pro Arg Asp Gly Phe Phe Gly Asn Pro Arg Lys Ser Lys Leu Ile
         260                 265                 270

Cys Gln Ala Thr Gly Phe Ser Pro Arg Gln Ile Gln Val Ser Trp Leu
     275                 280                 285

Arg Glu Gly Lys Gln Val Gly Ser Gly Val Thr Thr Asp Gln Val Gln
290                 295                 300

Ala Glu Ala Lys Glu Ser Gly Pro Thr Thr Tyr Lys Val Thr Ser Thr
305                 310                 315                 320

Leu Thr Ile Lys Glu Ser Asp Trp Leu Gly Gln Ser Met Phe Thr Cys
             325                 330                 335

Arg Val Asp His Arg Gly Leu Thr Phe Gln Gln Asn Ala Ser Ser Met
         340                 345                 350

Cys Val Pro Asp Gln Asp Thr Ala Ile Arg Val Phe Ala Ile Pro Pro
     355                 360                 365

Ser Phe Ala Ser Ile Phe Leu Thr Lys Ser Thr Lys Leu Thr Cys Leu
370                 375                 380

Val Thr Asp Leu Thr Thr Tyr Asp Ser Val Thr Ile Ser Trp Thr Arg
385                 390                 395                 400

Gln Asn Gly Glu Ala Val Lys Thr His Thr Asn Ile Ser Glu Ser His
             405                 410                 415

Pro Asn Ala Thr Phe Ser Ala Val Gly Glu Ala Ser Ile Cys Glu Asp
         420                 425                 430
```

-continued

```
Asp Trp Asn Ser Gly Glu Arg Phe Thr Cys Thr Val Thr His Thr Asp
        435                 440                 445

Leu Pro Ser Pro Leu Lys Gln Thr Ile Ser Arg Pro Lys Gly Val Ala
    450                 455                 460

Leu His Arg Pro Asp Val Tyr Leu Leu Pro Pro Ala Arg Glu Gln Leu
465                 470                 475                 480

Asn Leu Arg Glu Ser Ala Thr Ile Thr Cys Leu Val Thr Gly Phe Ser
                485                 490                 495

Pro Ala Asp Val Phe Val Gln Trp Met Gln Arg Gly Gln Pro Leu Ser
            500                 505                 510

Pro Glu Lys Tyr Val Thr Ser Ala Pro Met Pro Glu Pro Gln Ala Pro
        515                 520                 525

Gly Arg Tyr Phe Ala His Ser Ile Leu Thr Val Ser Glu Glu Trp
    530                 535                 540

Asn Thr Gly Glu Thr Tyr Thr Cys Val Val Ala His Glu Ala Leu Pro
545                 550                 555                 560

Asn Arg Val Thr Glu Arg Thr Val Asp Lys Ser Thr Gly Lys Pro Thr
                565                 570                 575

Leu Tyr Asn Val Ser Leu Val Met Ser Asp Thr Ala Gly Thr Cys Tyr
            580                 585                 590
```

<210> SEQ ID NO 3
<211> LENGTH: 723
<212> TYPE: DNA
<213> ORGANISM: Homo sapiens
<220> FEATURE:
<221> NAME/KEY: CDS
<222> LOCATION: (1)..(723)
<223> OTHER INFORMATION:

<400> SEQUENCE: 3

```
atg gtg ttg cag acc cag gtc ttc att tct ctg ttg ctc tgg atc tct      48
Met Val Leu Gln Thr Gln Val Phe Ile Ser Leu Leu Leu Trp Ile Ser
1               5                   10                  15 ggt gcc tac ggg gac atc gtg atg acc cag tct cca gac tcc ctg gct      96
Gly Ala Tyr Gly Asp Ile Val Met Thr Gln Ser Pro Asp Ser Leu Ala
            20                  25                  30 gtg tct ctg ggc gag agg gcc acc atc aac tgc aag tcc agc cag agt     144
Val Ser Leu Gly Glu Arg Ala Thr Ile Asn Cys Lys Ser Ser Gln Ser
        35                  40                  45 gtt tta tac agc tcc aac aat aag aac tac tta gct tgg tac cag cag     192
Val Leu Tyr Ser Ser Asn Asn Lys Asn Tyr Leu Ala Trp Tyr Gln Gln
    50                  55                  60 aaa cca gga cag cct cct aag ctg ctc att tac tgg gca tct acc cgg     240
Lys Pro Gly Gln Pro Pro Lys Leu Leu Ile Tyr Trp Ala Ser Thr Arg
65                  70                  75                  80 gaa tcc ggg gtc cct gac cga ttc agt ggc agc ggg tct ggg aca gat     288
Glu Ser Gly Val Pro Asp Arg Phe Ser Gly Ser Gly Ser Gly Thr Asp
                85                  90                  95 ttc act ctc acc atc agc agc ctg cag gct gaa gat gtg gca gtt tat     336
Phe Thr Leu Thr Ile Ser Ser Leu Gln Ala Glu Asp Val Ala Val Tyr
            100                 105                 110 tac tgt cag caa tat tat agt act cct ccg acg ttc ggc caa ggg acc     384
Tyr Cys Gln Gln Tyr Tyr Ser Thr Pro Pro Thr Phe Gly Gln Gly Thr
        115                 120                 125 aag gtg gaa atc aaa cga act gtg gct gca cca tct gtc ttc atc ttc     432
Lys Val Glu Ile Lys Arg Thr Val Ala Ala Pro Ser Val Phe Ile Phe
    130                 135                 140
```

```
ccg cca tct gat gag cag ttg aaa tct gga act gcc tct gtt gtg tgc      480
Pro Pro Ser Asp Glu Gln Leu Lys Ser Gly Thr Ala Ser Val Val Cys
145                 150                 155                 160 ctg ctg aat aac ttc tat ccc aga gag gcc aaa gta cag tgg aag gtg      528
Leu Leu Asn Asn Phe Tyr Pro Arg Glu Ala Lys Val Gln Trp Lys Val
                165                 170                 175 gat aac gcc ctc caa tcg ggt aac tcc cag gag agt gtc aca gag cag      576
Asp Asn Ala Leu Gln Ser Gly Asn Ser Gln Glu Ser Val Thr Glu Gln
            180                 185                 190 gac agc aag gac agc acc tac agc ctc agc agc acc ctg acg ctg agc      624
Asp Ser Lys Asp Ser Thr Tyr Ser Leu Ser Ser Thr Leu Thr Leu Ser
        195                 200                 205 aaa gca gac tac gag aaa cac aaa gtc tac gcc tgc gaa gtc acc cat      672
Lys Ala Asp Tyr Glu Lys His Lys Val Tyr Ala Cys Glu Val Thr His
210                 215                 220 cag ggc ctg agc tcg ccc gtc aca aag agc ttc aac agg gga gag tgt      720
Gln Gly Leu Ser Ser Pro Val Thr Lys Ser Phe Asn Arg Gly Glu Cys
225                 230                 235                 240 tag                                                                   723
```

<210> SEQ ID NO 4
<211> LENGTH: 240
<212> TYPE: PRT
<213> ORGANISM: Homo sapiens

<400> SEQUENCE: 4

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240
```

```
<210> SEQ ID NO 5
<211> LENGTH: 480
<212> TYPE: DNA
<213> ORGANISM: Homo sapiens
<220> FEATURE:
<221> NAME/KEY: CDS
<222> LOCATION: (1)..(480)
<223> OTHER INFORMATION:

<400> SEQUENCE: 5 atg aag aac cat ttg ctt ttc tgg gga gtc ctg gcg gtt ttt att aag        48
Met Lys Asn His Leu Leu Phe Trp Gly Val Leu Ala Val Phe Ile Lys
1               5                   10                  15 gct gtt cat gtg aaa gcc caa gaa gat gaa agg att gtt ctt gtt gac        96
Ala Val His Val Lys Ala Gln Glu Asp Glu Arg Ile Val Leu Val Asp
                20                  25                  30 aac aaa tgt aag tgt gcc cgg att act tcc agg atc atc cgt tct tcc       144
Asn Lys Cys Lys Cys Ala Arg Ile Thr Ser Arg Ile Ile Arg Ser Ser
            35                  40                  45 gaa gat cct aat gag gac att gtg gag aga aac atc cga att att gtt       192
Glu Asp Pro Asn Glu Asp Ile Val Glu Arg Asn Ile Arg Ile Ile Val
        50                  55                  60 cct ctg aac aac agg gag aat atc tct gat ccc acc tca cca ttg aga       240
Pro Leu Asn Asn Arg Glu Asn Ile Ser Asp Pro Thr Ser Pro Leu Arg
65                  70                  75                  80 acc aga ttt gtg tac cat ttg tct gac ctc tgt aaa aaa tgt gat cct       288
Thr Arg Phe Val Tyr His Leu Ser Asp Leu Cys Lys Lys Cys Asp Pro
                85                  90                  95 aca gaa gtg gag ctg gat aat cag ata gtt act gct acc cag agc aat       336
Thr Glu Val Glu Leu Asp Asn Gln Ile Val Thr Ala Thr Gln Ser Asn
                100                 105                 110 atc tgt gat gaa gac agt gct aca gag acc tgc tac act tat gac aga       384
Ile Cys Asp Glu Asp Ser Ala Thr Glu Thr Cys Tyr Thr Tyr Asp Arg
            115                 120                 125 aac aag tgc tac aca gct gtg gtc cca ctc gta tat ggt ggt gag acc       432
Asn Lys Cys Tyr Thr Ala Val Val Pro Leu Val Tyr Gly Gly Glu Thr
        130                 135                 140 aaa atg gtg gaa aca gcc tta acc cca gat gcc tgc tat cct gac taa       480
Lys Met Val Glu Thr Ala Leu Thr Pro Asp Ala Cys Tyr Pro Asp
145                 150                 155

<210> SEQ ID NO 6
<211> LENGTH: 159
<212> TYPE: PRT
<213> ORGANISM: Homo sapiens

<400> SEQUENCE: 6

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
        50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95
```

```
Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155

<210> SEQ ID NO 7
<211> LENGTH: 24
<212> TYPE: DNA
<213> ORGANISM: Artificial
<220> FEATURE:
<223> OTHER INFORMATION: an artificially synthesized sequence

<400> SEQUENCE: 7
ccaacggcaa caaagaaaag aacg                                          24

<210> SEQ ID NO 8
<211> LENGTH: 24
<212> TYPE: DNA
<213> ORGANISM: Artificial
<220> FEATURE:
<223> OTHER INFORMATION: an artificially synthesized sequence

<400> SEQUENCE: 8
aacatgctct ggccgagcca gtcg                                          24

<210> SEQ ID NO 9
<211> LENGTH: 24
<212> TYPE: DNA
<213> ORGANISM: Artificial
<220> FEATURE:
<223> OTHER INFORMATION: an artificially synthesized sequence

<400> SEQUENCE: 9
gcaagtccag ccagagtgtt ttat                                          24

<210> SEQ ID NO 10
<211> LENGTH: 24
<212> TYPE: DNA
<213> ORGANISM: Artificial
<220> FEATURE:
<223> OTHER INFORMATION: an artificially synthesized sequence

<400> SEQUENCE: 10
ctgtccttgc tgtcctgctc tgtg                                          24

<210> SEQ ID NO 11
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 11
aacagctcga gccaccatgg agtttgggct gag                                33

<210> SEQ ID NO 12
<211> LENGTH: 32
<212> TYPE: DNA
<213> ORGANISM: Artificial
<220> FEATURE:
<223> OTHER INFORMATION: an artificially synthesized primer sequence
```

-continued

```
<400> SEQUENCE: 12
agcggccagc cgccccgagc ctgtcgacag gc                                     32

<210> SEQ ID NO 13
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 13
atagaattcc accatggtgt tgcagaccca gg                                     32

<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
ggagcaggcg gccgcacttc tccctctaac                                        30

<210> SEQ ID NO 15
<211> LENGTH: 24
<212> TYPE: DNA
<213> ORGANISM: Artificial
<220> FEATURE:
<223> OTHER INFORMATION: an artificially synthesized sequence

<400> SEQUENCE: 15
accattgaga accagatttg tgta                                              24

<210> SEQ ID NO 16
<211> LENGTH: 24
<212> TYPE: DNA
<213> ORGANISM: Artificial
<220> FEATURE:
<223> OTHER INFORMATION: an artificially synthesized sequence

<400> SEQUENCE: 16
tgtgtagcac ttgtttctgt cata                                              24

<210> SEQ ID NO 17
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 17
atgaattcca ccatgaagaa ccatttgc                                          28

<210> SEQ ID NO 18
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 18
tatctagatt agtcaggata gcaggc                                            26
```

METHODS FOR STABILIZING PROTEIN SOLUTIONS

CROSS-REFERENCE TO RELATED APPLICATIONS

This application is the National Stage of International Application No. PCT/JP2004/014919, filed on Oct. 8, 2004, which claims the benefit of Japanese Patent Application Serial No. 2003-351410, filed on Oct. 9, 2003. The contents of both of the foregoing applications are hereby incorporated by reference in their entireties.

TECHNICAL FIELD

The present invention relates to methods for stabilizing proteins at low temperature.

BACKGROUND ART

Many higher animals have five different classes of immunoglobulins, IgG, IgA, IgM, IgD, and IgE. Each immunoglobulin class differs in properties such as size, charge, amino acid composition, and sugar content. Of these classes, IgM accounts for approximately 10% of all plasma immunoglobulins. IgM is the major component of early antibodies produced against cell-membrane antigens, infectious microorganisms, or soluble antigens, which have a complex antigenicity.

Human IgMs usually have a pentameric structure. Each of the five subunits constituting this pentameric structure has a four-stranded structure similar to that of IgG. The amino acid sequence of the μ chain, which is the heavy chain of IgM, is different from that of the γ chain, which is the heavy chain of IgG. The following differences can also be seen:

The μ chain has an extra constant domain than the γ chain.
The μ chain has four more oligosaccharide chains than the γ chain.

IgM has a polypeptide chain called the J chain, which is not found in IgG. The J chain is considered to assist the association of μ chains prior to secretion of IgM from antibody producing cells.

With advances in monoclonal antibody technology and recombinant DNA technology, large-scale production of pure immunoglobulins has become possible in recent years. Furthermore, gene recombination techniques have enabled production of chimeric antibodies and humanized antibodies. Chimeric antibodies are antibodies having a structure in which the variable regions have been replaced with variable regions derived from a different species. For example, "chimeric antibodies" comprising variable regions of non-human antibodies and the constant regions of human antibodies (Non-Patent Document 1/Proc. Natl. Acad. Sci. U.S.A., (1984) 81:6851) are known. Also known are humanized antibodies in which the complementarity determining regions (CDR) of other animal species are transferred into human immunoglobulins (Non-Patent Document 2/Nature (1986) 321:522-525)

Actual examples of antitumor antibodies are the anti-CD20 human chimeric antibody Rituxan (IDEC), and the anti-HER2/neu humanized antibody Herceptin (Genentech), which have completed clinical trials and have already been approved. These antibodies are now commercially available. Antibody-dependent cellular cytotoxicity (hereinafter referred to as ADCC) activity and complement-dependent cytotoxicity (hereinafter referred to as CDC) activity are known as effector functions of IgG and IgM. Since IgM has a higher CDC activity compared to IgG, it has an extremely high chance of becoming an anti-tumor antibody having CDC activity as its main effect. However, as described above, unlike IgG, IgM forms a multimer. Therefore, industrial scale production of recombinant IgM had been considered difficult.

IgM is also very unstable compared to IgG and has a low solubility. Therefore, the production of a highly concentrated and stable IgM solution is difficult. For example, Cytotherapy, 2001, 3(3), 233-242 (Non-Patent Document 5) reports that, even when IgM had been stored at −20° C., precipitation and decrease of activity occurred upon thawing. Furthermore, according to the report, IgM easily aggregates and precipitates during storage. Arch. Pathol. Lab. Med., 1999, 123, 119-125 (Non-Patent Document 6) showed that among precipitates called cryoprecipitations or low-temperature precipitations observed in human serum, Type I cryoglobulin, which produces a precipitate consisting of a single antibody component, is mainly IgM. IgM, in particular, readily undergoes cryoprecipitation, making it difficult to obtain a highly concentrated IgM solution at a low temperature. Most biopharmaceuticals are stored and distributed under refrigeration at around 4° C. to ensure stability. Since some IgMs cryoprecipitate at around 4° C., it is preferable that their cryoprecipitation is suppressed during drug formulation, storage, and distribution. Cryoprecipitation also occurs in IgM bulk drug substance production processes leading to formulation, during purification and concentration steps at low temperature, and during low-temperature storage between the multiple steps involved. This causes operational problems, and thus, it is preferable to suppress cryoprecipitation even in these circumstances.

Various attempts have been made to stabilize IgM at low temperature. For example, Immunochemistry, 1978, 15, 171-187 (Non-Patent Document 3) discloses that cryoprecipitation of IgM takes place more readily with temperature decrease and concentration increase. It also discloses that cryoprecipitation takes place in the pH range of 5 to 10, and that this cryoprecipitation can be avoided at extremely high pH or low pH. However, antibodies generally tend to undergo a deamidation reaction and aggregation at high pH, and denaturation and aggregation at low pH. Antibodies are generally known to be chemically and physically stable from pH5 to pH8, especially near pH5 to pH7. It is therefore difficult to ensure a stability sufficient enough to withstand pharmaceutical use at extremely high pH or low pH.

Journal of Biological Chemistry, 1977, 252(22), 8002-8006 (Non-Patent Document 4) examined the effect of various compounds on cryoprecipitation (solubility of IgM at low temperature), and discloses that cryoprecipitation decreases when sugars are added or salt concentration is increased. However, this disclosure shows that for effective prevention of cryoprecipitation using any sugars or salts, the sugars or salts must be added at high concentrations of approximately 500 mM or higher. When used as a pharmaceutical, it is preferable to achieve such an effect at lower concentrations.

WO 91/18106 (Patent Document 1) discloses methods for preventing cryoprecipitation by changing the structure of sugar chains attached to IgM. However, when sugar chains of antibodies are modified, in some cases, the binding activities of antibodies change. Therefore, it is desirable to develop methods for suppressing cryoprecipitation without altering the structure of antibodies, including their sugar chains.

Patent Document 1: WO 91/18106

Non-Patent Document 1: Proc. Natl. Acad. Sci. U.S.A, (1984) 81: 6851

Non-Patent Document 2: Nature (1986) 321: 522-525

Non-Patent Document 3: Immunochemistry, 1978, 15, 171-187

Non-Patent Document 4: Journal of Biological Chemistry, 1977, 252(22), 8002-8006

Non-Patent Document 5: Cytotherapy, 2001, 3(3), 233-242

Non-Patent Document 6: Arch. Pathol. Lab. Med., 1999, 123, 119-125

DISCLOSURE OF THE INVENTION

The present invention was achieved in view of the above circumstances. An objective of the present invention is to stabilize proteins in solution at low temperature. More specifically, the present invention aims to stabilize proteins under conditions (such as pH and salt concentration) that withstand pharmaceutical use.

To solve the above-mentioned problems, the present inventors examined the use of a citric acid buffer as a pH buffer, in the pH range of 5 to 8 where antibodies are generally considered to be stable, as a method for suppressing cryoprecipitation of IgM at a pH range and salt concentration suitable for IgM storage. As a result, the citric acid buffer was found to significantly suppress cryoprecipitation. More specifically, the use of citric acid buffer enhanced the solubility of IgM at low temperature, and enabled preparation of highly concentrated IgM solutions. This effect of citric acid on IgM is caused by adjustment of the strength of protein-protein interactions such as ionic interactions, van der Waals interactions, and hydrogen bonds. Accordingly, in addition to IgM, this effect can be accomplished in various other proteins that show decreased solubility in aqueous solutions at low temperature.

Specifically, the present invention relates to methods for stabilizing proteins at low temperature; more specifically the present invention provides the following:

(1) a method for stabilizing a protein at low temperature, wherein the method comprises adding a citric acid buffer to a solution comprising the protein;

(2) the method of (1), wherein the protein is stabilized by suppressing cryoprecipitation;

(3) the method of (1), wherein the protein is IgM; and (4) the method of (1), wherein pH of the solution comprising the protein is 5 to 8.

DETAILED DESCRIPTION

Figure 1:
FIG. 1 is a set of photographs showing the effect of citric acid buffer on the stability of IgM at various concentrations at low temperature (4° C.).
Figure 1:
Figure 1:
Figure 1:
Figure 1:
Figure 1:
Figure 1:
Figure 1:
Figure 1:
Figure 1:

In the present invention, the term "proteins" refers to compounds in which amino acids are linked to each other through peptide bonds. Any protein whose solubility in aqueous solutions is decreased at low temperatures is suitable for the present invention, examples being IgG and peanut agglutinin (PNA).

IgM is particularly preferred as a protein in the present invention. In the present invention, the term "IgM" refers to an immunoglobulin that comprises constant regions of the μ chain as the constant regions of the heavy chains, and forms a pentameric or hexameric structure. The origin of the variable regions constituting the IgM of the present invention is not limited. Therefore, in addition to a variable region derived from the μ chain, the IgM of the present invention may comprise a variable region derived from IgG, or a partial structure thereof. The partial structure of a variable region can comprise the framework and CDR. The "IgM" in the present invention refers to expression products of exogenous IgM genes introduced into cells for transformation.

Furthermore, the constant regions constituting the IgM of the present invention may be derived from any animal species. That is, the IgM of the present invention comprises an IgM constant region derived from any type of animal species carrying an IgM-type immunoglobulin. When IgM is administered in vivo, at least its constant regions are preferably derived from an animal species same as the species to which the IgM is administered. Therefore, when the IgM is administered to humans, at least its constant regions are preferably derived from humans. IgM composed of constant regions derived from humans, and variable regions derived from another animal species or another human, is called a chimeric antibody. A more preferable IgM for administration to humans is an IgM whose variable region framework is derived from humans, in addition to the constant regions. Human antibodies which have retained the variable region framework structure, but only the CDR has been replaced with that of an antibody from another animal species are called humanized antibodies.

Cryoprecipitation of highly concentrated proteins can be suppressed by the present invention. Herein, "highly concentrated" refers to a concentration in solution higher than 1 mg/mL (for example, 5 mg/mL or more, 10 mg/mL or more, 20 mg/mL or more, or 25 mg/mL or more).

"Citric acid buffers" that may be used in the present invention are not limited to buffers that utilize only citric acid as the pH buffering agent, and may comprise pH buffering agents such as phosphoric acid other than citric acid.

The concentration of citric acid buffer added to solutions is usually 1 mM to 500 mM, preferably 5 mM to 100 mM, and more preferably 10 mM to 50 mM. The term "stabilization" in the present invention refers to suppressing the increase of cryoprecipitated proteins in solutions.

The stability of protein solutions can be determined, for example, from the cryoprecipitation increase suppression rate that can be derived from the following formula.

Suppression ratio of cryoprecipitation increase= $(A-B)/A \times 100$

A: cryoprecipitate formation ratio in a highly concentrated IgM solution to which a citric acid buffer has not been added (Control)

B: cryoprecipitate formation ratio in a highly concentrated IgM solution to which a citric acid buffer has been added (Test sample)

The solutions of the present invention have a cryoprecipitation increase suppression rate of preferably 10% or more, more preferably 30% or more, even more preferably 50% or more, and yet even more preferably 80% or more, after adding a citric buffer and keeping at 1° C. for a week.

The pH of the protein-comprising solutions of this invention can be adjusted to a value at which proteins are stable, and specifically, pH5 to pH8 is preferable. Furthermore, the pH of the protein-comprising solutions of this invention can be adjusted to a value suitable for stable storage of the proteins, and specifically, pH5 to pH7 is preferable, while pH5 to pH6 is more preferable.

The dosage form of pharmaceutical formulations of the present invention is not particularly limited, and any discretionary dosage form is possible. Examples of the dosage form include a solution formulation and a lyophilized formulation. Examples of the solution formulations include formulations stored in a cold place, formulations stored at room temperature, and frozen formulations. There are no particular limitations on the administration route for the pharmaceutical formulations of the present invention; any administration route can be used. The pharmaceutical formulations may thus be administered either orally or parenterally depending on the purpose of use.

Specific dosage forms for parenteral administration include injections, and dosage forms for nasal administration, pulmonary administration, and transdermal administration. Systemic or local injections can be carried out by intravenous injections, intramuscular injections, peritoneal injections, subcutaneous injections, or such.

In addition to administering directly to patients as is, IgM stabilized by methods of the present invention can be administered as pharmaceutical agents formulated by well-known pharmaceutical methods. For example, the stabilized IgM can be used as sterile solutions prepared with water or other pharmaceutically acceptable liquid, or as injections of suspensions. Furthermore, it may be formulated by, for example, appropriately combining with pharmaceutically acceptable carriers or media, such as sterilized water, saline, emulsifiers, suspending agents, surfactants, stabilizers, vehicles, and preservatives, and mixing them at a unit dosage form required for generally accepted pharmaceutical practice. The amount of active ingredient in these formulations can be adjusted so that an appropriate dose within an indicated range can be acquired.

Sterile compositions for injections can be formulated according to usual pharmaceutical practice using vehicles such as distilled water for injections. Examples of aqueous solutions used for injections include physiological saline and isotonic solutions comprising glucose and other auxiliary agents. Specifically, the auxiliary agents may be D-sorbitol, D-mannose, D-mannitol, sodium chloride, and such. Suitable solubilizers may also be added to pharmaceutical compositions. For example, alcohols and non-ionic surfactants are preferred solubilizers. Specific examples of alcohols comprise ethanol, polyalcohols such as propylene glycol and polyethylene glycol. Examples of non-ionic surfactants may be Polysorbate80 or HCO-50. Cationic surfactants such as benzalkonium chloride may also be used.

Oily fluids may be, for example, sesame oil and soybean oil, and may be used together with benzyl benzoate or benzyl alcohol as a solubilizer. Furthermore, buffers such as phosphate buffer and sodium acetate buffer, analgesic agents such as procain hydrochloride, stabilizers such as benzyl alcohol and phenol, and antioxidants may be combined. The prepared injections are usually loaded into suitable vials or ampules.

The administration dose of the pharmaceutical formulations can be appropriately selected according to the disease to be treated, and age and symptoms of the patient. For example, a single dose can be selected within the range of 0.0001 mg to 1,000 mg per 1 kg body weight. Alternatively, for example, the dose can be selected within the range of 0.001 to 100,000 mg/body of patient. However, doses of the pharmaceutical formulations of the present invention are not limited to these.

One can refer to WO 2002/096457 for the preparation of liquid formulations and such of the present invention.

All prior art literature cited herein are incorporated herein by reference.

EXAMPLES

Hereinafter, the present invention is specifically illustrated with reference to Examples, but it is not to be construed as being limited thereto.

Example 1

In the following Examples, recombinant anti-ganglioside GM3 human antibody produced in the Reference Example (hereinafter, referred to as "MABON-01") was used as the IgM. Highly concentrated MABON-01 solutions were produced at room temperature. The compositions of the solutions were as follows:

Citric acid buffer: 20 mM sodium citrate, 300 mM NaCl, pH5.5 (citric acid buffer)

Acetic acid buffer: 20 mM sodium acetate, 300 mM NaCl, pH5.5 (acetic acid buffer)

IgM-comprising citric acid buffers and acetic acid buffers were named as shown in Table 1 for convenience according to the concentration of IgM.

TABLE 1

| MABON-01 | Acetic acid buffers | Citric acid buffers |
| --- | --- | --- |
| 50 mg/mL | A5 | C5 |
| 33 mg/mL | A4 | C4 |
| 25 mg/mL | A3 | C3 |
| 17 mg/mL | A2 | C2 |
| 8 mg/mL | A1 | C1 |

These solutions stored at 4° C. are shown in FIG. 1. Whereas cryoprecipitation was clearly observed in the acetic acid buffer A4 and A5 comprising highly concentrated MABON-01, cryoprecipitation was not observed in citric acid buffer solutions (C4 and C5) comprising the same concentration of MABON-01. This revealed that use of citric acid as the buffer enables preparation of highly concentrated solutions with no cryoprecipitation.

Example 2

An approximately 20 mg/mL solution of MABON-01 in a 20 mM sodium acetate, 300 mM NaCl, pH 6.0 solution was prepared at room temperature, and dialyzed at 4° C. against 20 mM sodium citrate, 300 mM NaCl, pH5.5 (citric acid acid buffer), or 20 mM sodium acetate, 300 mM NaCl, pH6.0 (acetic acid buffer) using a dialyzer membrane EasySep (TOMY) to exchange the buffer. After warming to room temperature, the solutions were diluted using each corresponding buffer to prepare 10 mg/mL solutions. These solutions were placed in 0.5-mL PCR tubes, and stored for 26 days at 7° C., 4° C., or 1° C. Cryoprecipitate formation was then visually observed. After centrifugation, the MABON-01 concentrations in the obtained supernatants were determined by gel filtration chromatography. In the gel filtration chromatography, a G4000SW$_{XL}$ (TOSOH) column was used, and a 50 mM sodium phosphate, 500 mM KCl, pH7.4 solution was used as the mobile phase. The values of the sum of the aggregate peak area and the monomer peak area before and after cryoprecipitation as determined by gel filtration chromatography were compared, and the cryoprecipitate formation rate of MABON-01 was calculated.

Visually, cryoprecipitation was observed when the MABON-01 solution in acetic acid buffer was stored at 4° C. and 1° C., but not in other solutions.

Figure 2:
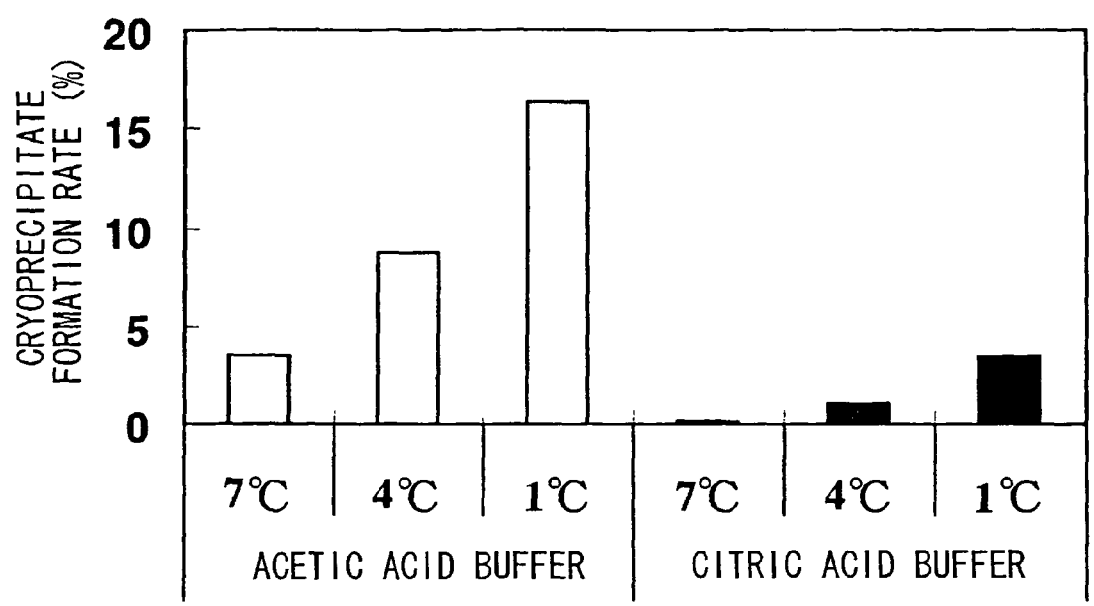
FIG. 2 shows the effect of citric acid buffer on the stability of 10 mg/mL IgM solutions at low temperature (1° C., 4° C., and 7° C.).

The cryoprecipitate formation ratio in each sample is shown in FIG. 2. In all buffer systems, the tendency was that the lower the temperature, the higher the level of precipitation. However, at all temperatures, the precipitation amount was lower in the citric acid buffer systems than in the acetic acid buffer systems, confirming a clear cryoprecipitation suppression effect due to the use of a citric acid buffer. Changing the buffer from 20 mM acetic acid buffer to 20 mM citric acid buffer showed that it is possible to store at lower temperatures without adding high concentrations of salts or such.

Example 3

An approximately 20 mg/mL solution of MABON-01 in a 20 mM sodium acetate, 300 mM NaCl, pH 6.0 solution was prepared at room temperature, and dialyzed at 4° C. against 20 mM sodium citrate, 300 mM NaCl, pH5.0, pH5.5, or pH6.0 (citric acid buffer), or 20 mM sodium acetate, 300 mM NaCl, pH5.0, pH5.5, or pH6.0 (acetic acid buffer), using a dialyzer membrane EasySep (TOMY), to exchange the buffer. After heating to room temperature, the solutions were diluted using each corresponding buffer to prepare 10 mg/mL solutions. These solutions were placed in 0.5-mL PCR tubes, and stored for 29 days at 4° C. Cryoprecipitate formation was then visually observed. After centrifugation, the MABON-01 concentrations in the obtained supernatants were determined by gel filtration chromatography. In the gel filtration chromatography, a G4000SW$_{XL}$ (TOSOH) column was used, and a 50 mM sodium phosphate, 500 mM KCl, pH7.4 solution was used as the mobile phase. The values of the sum of the aggregate peak area and the monomer peak area before and after cryoprecipitation as determined by gel filtration chromatography were compared, and the cryoprecipitate formation rate of MABON-01 was calculated.

Figure 3:
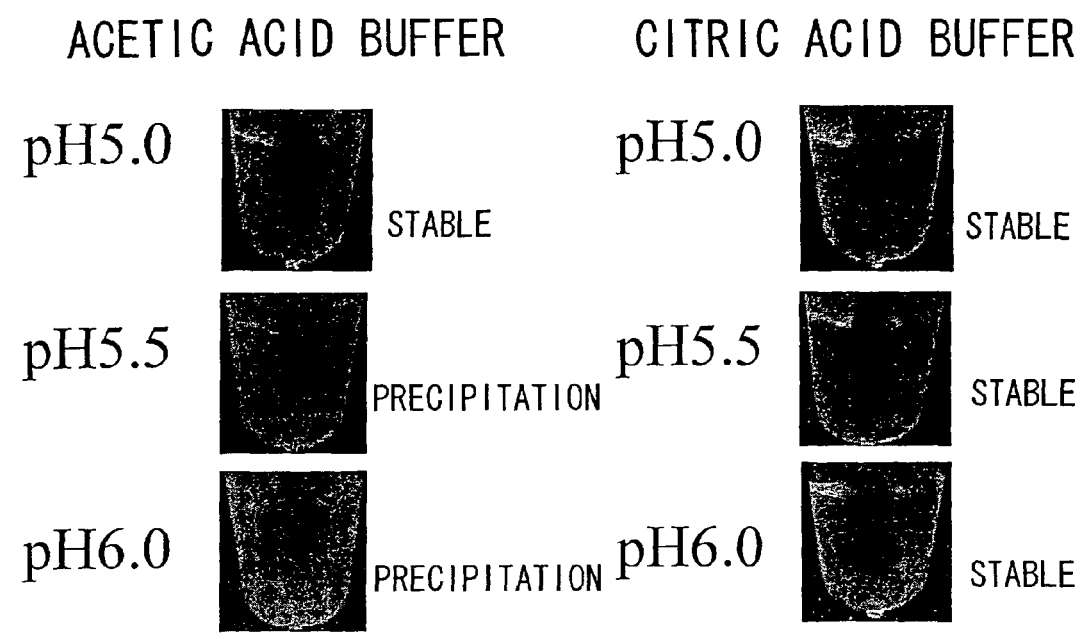
FIG. 3 is a set of photographs showing the effect of citric acid buffer on the stability of 10 mg/mL IgM solutions at low temperature (4° C.).

Visual observations of the solutions are shown in FIG. 3. Cryoprecipitation was observed in acetic acid buffers at pH5.5 and pH6.0, but no precipitation was observed in any other solutions.

Figure 4:
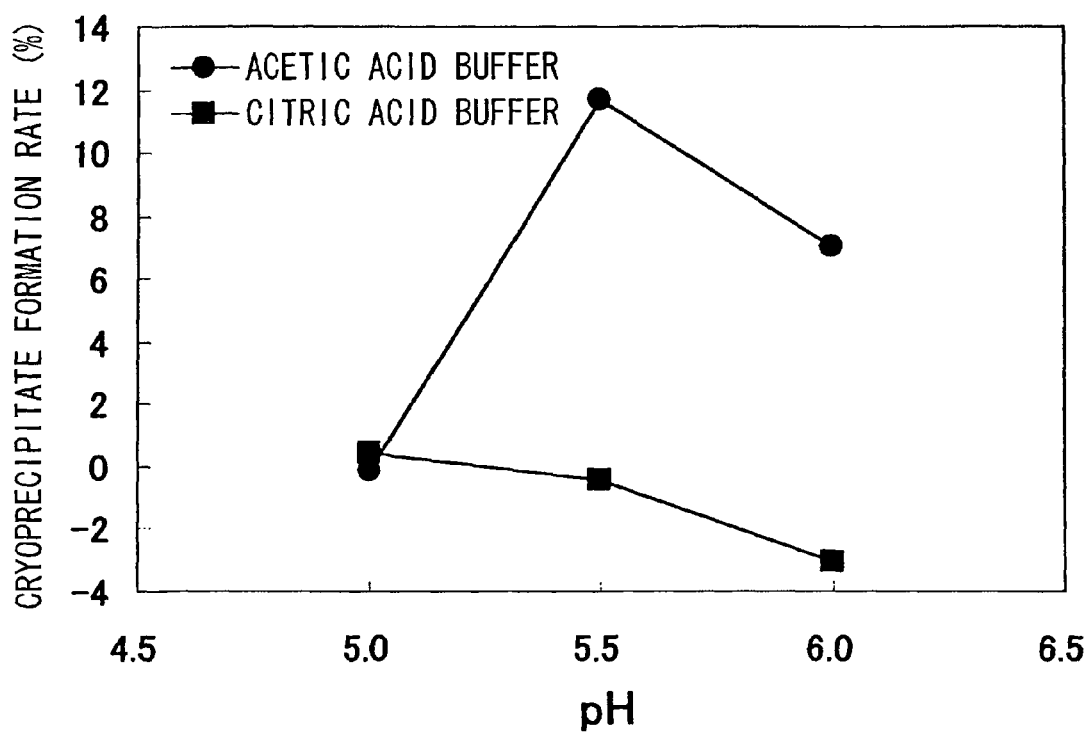
FIG. 4 shows the effect of citric acid buffer on the stability of 10 mg/mL IgM solutions at low temperature (4° C.).

The cryoprecipitate formation ratio is shown in FIG. 4. Whereas the acetic acid buffer system showed a curve that reaches a maximum at pH5.5, the citric acid buffer system had low level of precipitates and a particular tendency was not observed. When comparisons were made within pH5.5 to pH6.0, which is the most suitable pH range for pharmaceutical preparations, changing from a 20 mM acetic acid buffer solution system to a 20 mM citric acid buffer system suppressed cryoprecipitation even when the pH was kept at the same value.

Reference Example 1

Production of Recombinant Human Antibodies Against Ganglioside GM3

1.1 Construction of Anti-Ganglioside GM3 Human Antibody Heavy Chain Gene

A gene encoding the heavy chain of a human antibody that binds to ganglioside GM3 was amplified by RT-PCR using total RNAs extracted from human B cells transformed with Epstein-Barr virus (hereinafter, denoted as anti-ganglioside GM3 human antibody-expressing B cells).

Total RNAs were extracted from $1 \times 10^7$ anti-ganglioside GM3 human antibody-expressing B cells using RNeasy Plant Mini Kit (QIAGEN). Two oligonucleotides (LMH-f3 and LMH-r3) were designed based on the nucleotide sequence of anti-ganglioside GM3 human antibody gene reported by Hoon et al. (Cancer Research 1993; 53: 5244-5250). LMH-f3 (SEQ ID NO: 7) was synthesized in the sense direction, and LMH-r3 (SEQ ID NO: 8) was synthesized in the antisense direction. Using 1 µg of total RNAs, gene fragments were amplified separately for the 5' end and the 3' end by SMART RACE cDNA Amplification Kit (CLONTECH). Synthetic oligonucleotides LMH-r3 and LMH-f3 were used for amplifying the 5' and 3' ends of the gene, respectively. Reverse transcription reaction was carried out at 42° C. for 1.5 hours.

The composition of the PCR reaction solution (50 µL) is shown below:
5 µL of 10× Advantage 2 PCR Buffer,
5 µL of 10× Universal Primer A Mix,
0.2 mM dNTPs (DATP, dGTP, dCTP, and dTTP),
1 µL of Advantage 2 Polymerase Mix,
  (All the above were from CLONTECH)
2.5 µL of reverse transcription product, and
10 pmol of synthetic oligonucleotide LMH-f3 or LMH-r3.

The reaction was carried out under the conditions of:
94° C. (initial temperature) for 30 seconds,
5 cycles of 94° C. for 5 seconds and 72° C. for 3 minutes,
5 cycles of 94° C. for 5 seconds, 70° C. for 10 seconds, and 72° C. for 3 minutes,
25 cycles of 94° C. for 5 seconds, 68° C. for 10 seconds, and 72° C. for 3 minutes, and finally 72° C. for 7 minutes.

The PCR products were purified from agarose gel using QIAquick Gel Extraction Kit (QIAGEN), and then cloned into pGEM-T Easy vector (Promega). After sequencing, an approximately 1.1 kbp fragment was obtained by digesting the vector comprising the 5' end of the gene using restriction enzymes ApaI (Takara Shuzo) and SacII (Takara Shuzo), while an approximately 1.1 kbp fragment was obtained by digesting the vector comprising the 3' end of the gene using restriction enzymes ApaI (Takara Shuzo) and NotI (Takara Shuzo). The fragments were then mixed, and cloned into pBluescript KS+ vector (TOYOBO) to obtain a full-length anti-ganglioside GM3 human antibody heavy chain gene.

To clone into vectors for expression in animal cells, full-length gene fragments were amplified using synthetic oligonucleotides LMH-fxho and LMH-rsal. LMH-fxho (SEQ ID NO: 11) is a forward primer designed to hybridize to the 5' end of the anti-ganglioside GM3 human antibody heavy chain gene, and to comprise an XhoI restriction enzyme recognition sequence and a Kozak sequence. LMH-rsal (SEQ ID NO: 12) is a reverse primer designed to hybridize to the 3' end of the anti-ganglioside GM3 human antibody heavy chain gene, and to comprise a SalI restriction enzyme recognition sequence.

The composition of the PCR reaction solution (50 μL) is shown below:
- 5 μL of 10×PCR Buffer,
- 1 mM MgSO$_4$,
- 0.2 mM dNTPs (DATP, dGTP, dCTP, and dTTP),
- 1 unit of DNA polymerase KOD-Plus,
  (All the above were from TOYOBO)
- 10 ng of pBluescript KS+ vector comprising the full-length anti-ganglioside GM3 human antibody heavy chain gene, and
- 10 pmol of synthetic oligonucleotides LMH-fxho and LMH-rsal.

The reaction was carried out under conditions of:
- 94° C. (initial temperature) for 2 minutes,
- 30 cycles of 94° C. for 15 seconds, 60° C. for 30 seconds, and 68° C. for 2 minutes, and finally 72° C. for 5 minutes.

The amplified gene fragment was cloned by digesting with the XhoI restriction enzyme (Takara Shuzo) and the SalI restriction enzyme (Takara Shuzo), then purifying using QIAquick PCR Purification Kit (QIAGEN), and linking to the XhoI restriction enzyme site of pUCAG. This pUCAG vector is obtained by: linking the 2.6 kbp fragment obtained by digesting pCXN (Niwa et al., Gene 1991; 108: 193-200) using the BamHI restriction enzyme to the BamHI restriction enzyme site of pUC19 vector (TOYOBO). The obtained plasmid was named pUCAG/L612H. The nucleotide sequence and amino acid sequence of the anti-ganglioside GM3 human antibody heavy chain in this plasmid are shown in SEQ ID NOs: 1 and 2, respectively.

1.2 Construction of Anti-Ganglioside GM3 Human Antibody Light Chain Gene

A gene encoding the light chain of anti-ganglioside GM3 human antibody was amplified by RT-PCR using total RNAs extracted from the anti-ganglioside GM3 human antibody-expressing B cells. The total RNAs were extracted from the anti-ganglioside GM3 human antibody-expressing B cells in a manner similar to that mentioned above. Two oligonucleotides (LML-f1 and LML-r1) were designed based on the nucleotide sequence of anti-ganglioside GM3 human antibody gene reported by Hoon et al. (Cancer Research 1993; 53: 5244-5250). LML-f1 (SEQ ID NO: 9) and LML-r1 (SEQ ID NO: 10) were synthesized in the sense and antisense directions, respectively.

Using 1 μg of total RNAs, gene fragments were amplified separately for the 5' end and the 3' end by the SMART RACE cDNA Amplification Kit (CLONTECH). Synthetic oligonucleotides LML-r1 and LML-f1 were used for amplifying the 5' and 3' ends of the gene, respectively. Reverse transcription reaction was carried out at 42° C. for 1.5 hours.

The composition of the PCR reaction solution (50 μL) is shown below:
- 5 μL of 10× Advantage 2 PCR Buffer,
- 5 μL of 10× Universal Primer A Mix,
- 0.2 mM dNTPs (DATP, dGTP, dCTP, and dTTP),
- 1 μL of Advantage 2 Polymerase Mix,
  (All the above were from CLONTECH)
- 2.5 μL of reverse transcription product, and
- 10 pmol of synthetic oligonucleotide LML-f1 or LML-r1

The reaction was carried out under conditions of:
- 94° C. (initial temperature) for 30 seconds,
- 5 cycles of 94° C. for 5 seconds and 72° C. for 3 minutes,
- 5 cycles of 94° C. for 5 seconds, 70° C. for 10 seconds, and 72° C. for 3 minutes,
- 25 cycles of 94° C. for 5 seconds, 68° C. for 10 seconds, and 72° C. for 3 minutes, and finally 72° C. for 7 minutes.

PCR product was purified from the agarose gel using QIAquick Gel Extraction Kit (QIAGEN), and then cloned into pGEM-T Easy vector (Promega). After sequencing, an approximately 0.7 kbp fragment was obtained by digesting the vector comprising the 5' end of the gene using the EcoRI restriction enzyme (Takara Shuzo), while an approximately 0.9 kbp fragment was obtained by digesting the vector comprising the 3' end of the gene using the EcoRI restriction enzyme (Takara Shuzo). The two fragments were mixed, and used to amplify the full-length gene fragment using synthetic oligonucleotides LML-feco and LML-mot. LML-feco (SEQ ID NO: 13) is a forward primer, and was designed to hybridize to the 5' end of the anti-ganglioside GM3 human antibody light chain gene, and to comprise an EcoRI restriction enzyme recognition sequence and a Kozak sequence. LML-rnot (SEQ ID NO: 14) is a reverse primer, and was designed to hybridize to the 3' end of the anti-ganglioside GM3 human antibody light chain gene, and to comprise a NotI restriction enzyme recognition sequence.

The composition of the PCR reaction solution (50 μL) is shown below:
- 5 μL of 10×PCR Buffer,
- 1 mM MgSO$_4$,
- 0.2 mM dNTPs (DATP, dGTP, dCTP, and dTTP),
- 1 unit of DNA polymerase KOD-Plus,
  (All the above were from TOYOBO)
- 5'-end gene fragment,
- 3'-end gene fragment, and
- 10 pmol of synthetic oligonucleotides LML-feco and LML-rnot.

The reaction was carried out under conditions of:
- 94° C. (initial temperature) for 2 minutes,
- 30 cycles of 94° C. for 15 seconds, 60° C. for 30 seconds, and 68° C. for 2 minutes, and finally 72° C. for 5 minutes.

The amplified gene fragment was cloned by digesting with the EcoRI restriction enzyme (Takara Shuzo) and the NotI restriction enzyme (Takara Shuzo), then purifying using QIAquick PCR Purification Kit (QIAGEN) and linking to the EcoRI and NotI restriction enzyme cleavage sites of pCXND3.

The pCXND3 vector was constructed as follows: DHFR-ΔE-rvH-PM1-f (see WO 92/19759) was digested at the EcoRI/SmaI restriction enzyme site to separate their antibody heavy chain gene and vector region. Only the vector portion was then collected, into which the EcoRI-NotI-BamHI adaptor (Takara Shuzo) was cloned. This vector was named pCHOI.

A vector in which the DHFR gene expression site of pCHOI is cloned into the HindIII restriction enzyme site of pCXN (Niwa et al., Gene 1991; 108:193-200) was named pCXND3. Furthermore, the light-chain gene fragment was cloned into pCXND3 and the obtained plasmid was named pCXND3/L612L. The nucleotide sequence and amino acid sequence of anti-ganglioside GM3 human antibody light chain in this plasmid are shown in SEQ ID NOs: 3 and 4, respectively.

1.3 Construction of the Anti-Ganglioside GM3 Human Antibody Expression Vector

To produce the anti-ganglioside GM3 human antibody expression vector, pUCAG/L612H was digested with the HindIII restriction enzyme (Takara Shuzo), and the resulting an approximately 4.0 kbp fragment was linked to the HindIII restriction enzyme cleavage site of pCXND3/1612L. The obtained plasmid was named pCXND3/L612IgM. This plasmid expresses the neomycin-resistance gene, DHFR gene, and anti-ganglioside GM3 human antibody gene in animal cells.

1.4 Construction of Anti-Ganglioside GM3 Human Antibody J-Chain Gene and Expression Vector A gene encoding the J chain of anti-ganglioside GM3 human antibody was amplified by RT-PCR using total RNAs extracted from anti-ganglioside GM3 human antibody-expressing B cells. Total RNAs were extracted from anti-ganglioside GM3 human antibody-expressing B cells in a manner similar to that mentioned above. Two oligonucleotides (J-f1 and J-r1) were designed and synthesized based on the nucleotide sequence of the human antibody J chain gene registered in GenBank (GenBank accession number: M12759). J-f1 (SEQ ID NO: 15) hybridizes to human antibody J chain gene Exon 3 in the sense direction, and J-r1 (SEQ ID NO: 16) hybridizes to the human antibody J chain gene Exon 4 in the antisense direction.

Using 1 µg of total RNAs, gene fragments were amplified separately for the 5' end and the 3' end by the SMART RACE cDNA Amplification Kit (CLONTECH). Synthetic oligonucleotides J-r1 and J-f1 were used for amplifying the 5' and 3' ends of the gene, respectively. Reverse transcription reaction was carried out at 42° C. for 1.5 hours.

The composition of the PCR reaction solution (50 µL) is shown below:
    5 µL of 10× Advantage 2 PCR Buffer,
    5 µL of 10× Universal Primer A Mix,
    0.2 mM dNTPs (dATP, dGTP, dCTP, and dTTP),
    1 µL of Advantage 2 Polymerase Mix,
        (All the above were all from CLONTECH)
    2.5 µL of reverse transcription product, and
    10 pmol of synthetic oligonucleotide J-f1 or J-r1

The reaction was carried out under conditions of:
    94° C. (initial temperature) for 30 seconds,
    5 cycles of 94° C. for 5 seconds and 72° C. for 3 minutes,
    5 cycles of 94° C. for 5 seconds, 70° C. for 10 seconds, and 72° C. for 3 minutes,
    25 cycles of 94° C. for 5 seconds, 68° C. for 10 seconds, and 72° C. for 3 minutes, and finally 72° C. for 7 minutes.

PCR product was purified from the agarose gel using QIAquick Gel Extraction Kit (QIAGEN), and then cloned into pGEM-T Easy vector (Promega).

After sequencing, an approximately 0.5 kbp fragment was obtained by digesting the vector comprising the 5' end of the gene using the EcoRI restriction enzyme (Takara Shuzo), and an approximately 1.0 kbp fragment was obtained by digesting the vector comprising the 3' end of the gene using the EcoRI restriction enzyme (Takara Shuzo). The two fragments were mixed, and used to amplify the full-length gene fragment using synthetic oligonucleotides J-feco and J-rxba.

J-feco (SEQ ID NO: 17) is a forward primer designed to hybridize to the 5' end of the anti-ganglioside GM3 human antibody J chain gene, and to comprise an EcoRI restriction enzyme recognition sequence and a Kozak sequence. J-rxba (SEQ ID NO: 18) is a reverse primer designed to hybridize to the 3' end of the anti-ganglioside GM3 human antibody J chain gene, and to comprise an XbaI restriction enzyme recognition sequence.

The composition of the PCR reaction solution (50 µL) is shown below:
    5 µL of 10×PCR Buffer,
    1 mM MgSO$_4$,
    0.2 mM dNTPs (DATP, dGTP, dCTP, and dTTP),
    1 unit of DNA polymerase KOD-Plus,
        (the above-mentioned ingredients were all from TOYOBO)
    5'-end gene fragment,
    3'-end gene fragment, and
    10 pmol of synthetic oligonucleotides LML-feco and LML-rxba The reaction was carried out under conditions of:
    94° C. (initial temperature) for 2 minutes,
    30 cycles of 94° C. for 15 seconds, 60° C. for 30 seconds, and 68° C. for 2 minutes, and finally 72° C. for 5 minutes.

The amplified gene fragment was cloned by digesting with the EcoRI restriction enzyme (Takara Shuzo) and the XbaI restriction enzyme (Takara Shuzo), then purifying using QIAquick PCR Purification Kit (QIAGEN), and linking to the EcoRI and XbaI restriction enzyme cleavage sites of pCOSII-Zeo.

This pCOSII-Zeo vector is obtained by removing the DHFR gene expression site of pCHOI, and cloning the Zeocin-resistant gene expression site thereto. The obtained plasmid was named pCOSII-Zeo/J chain. The nucleotide sequence and amino acid sequence of anti-ganglioside GM3 human antibody J chain in this plasmid are shown in SEQ ID NOs: 5 and 6, respectively.

1.5 Expression of Anti-Anglioside GM3 Human Antibody Using Animal Cells

Stable expression cell lines derived from CHO cells (DG44 line) were produced as described below. Genes were introduced by electroporation using Gene Pulser II (BioRad).

Introduction of genes to obtain cell lines that do not express the J chain is described below. 0.75 mL of CHO cells suspended in PBS ($1 \times 10^7$ cells/mL) was mixed with anti-ganglioside GM3 human antibody expression vector pCXND3/L612IgM (25 µg), cooled on ice for 10 minutes, transferred to a cuvette, and then pulsed at 1.5 kV and 25 µFD.

After a recovery period of 10 minutes at room temperature, the electroporated cells were suspended in 40 mL of CHO-S-SFMII medium (Invitrogen) comprising 1×HT Supplement (Invitrogen). A 50-fold diluted solution was further prepared using the same medium, and then aliquoted at 100 µL/well into a 96-well culture plate. After incubation for 24 hours in a $CO_2$ incubator (5% $CO_2$), Geneticin (Invitrogen) was added to the wells at 0.5 mg/mL and cultured for 2 weeks.

The IgM levels in the culture supernatants of wells in which colonies of Geneticin-resistant transformants were found were measured by the concentration assay described in Reference Example 1.6. Cell lines highly expressing the anti-ganglioside GM3 human antibodies were successively expanded to obtain anti-ganglioside GM3 human antibody-expressing stable cell lines CA02, CA15, CA19, CA20, and CA24.

Introduction of genes to obtain cell lines expressing the J chain is described below. 0.75 mL of CHO cells suspended in PBS ($1 \times 10^7$ cells/mL) was mixed with anti-ganglioside GM3 human antibody expression vector pCXND3/L612IgM (25 µg) and J chain expression vector pCOSII-Zeo/J chain (20 µg), cooled on ice for 10 minutes, transferred to a cuvette, and then pulsed at 1.5 kV and 25 µFD.

After recovered for 10 minutes at room temperature, the electroporated cells were suspended in 40 mL of CHO-S-SFMII medium (Invitrogen) comprising 1×HT Supplement (Invitrogen).

A 50-fold diluted solution was further prepared using the same medium and aliquoted at 100 μL/well into a 96-well culture plate. After incubation for 24 hours in a $CO_2$ incubator (5% $CO_2$), 0.5 mg/mL Geneticin (Invitrogen) and 0.6 mg/mL Zeocin (Invitrogen) were added to wells, and cultured for 2 weeks. The IgM levels in the culture supernatants of wells in which colonies of Geneticin- and Zeocin-resistant transformants were found were measured by the concentration assay described in Reference Example 1.6. Cell lines highly expressing the anti-ganglioside GM3 human antibodies were successively expanded to obtain anti-ganglioside GM3 human antibody-expressing stable cell lines (CJ15, CJ25, CJ38, CJ45, and CJ67).

1.6 Measurement of IgM Concentration in Culture Supernatants

IgM concentration in the culture supernatants was measured as described below. Anti-Human IgM (BIOSOURCE) was diluted using a coating buffer (0.1 M $NaHCO_3$ and 0.02% $NaN_3$) to prepare a 1 μg/mL solution. The diluted solution was added to a 96-well ELISA plate at 100 μL/well, and then reacted at 4° C. for 24 hours or longer to coat the plate.

After washing the wells with Rinse Buffer, blocking was carried out by adding 200 μL/well of Diluent Buffer and reacting at room temperature for 1 hour or longer. Compositions of the Rinse Buffer and Diluent Buffer are shown below.

Rinse Buffer: PBS(−)
0.05% Tween20
Diluent Buffer: 50 mM Tris,
1 mM $MgCl_2$,
0.15 M NaCl,
0.05% Tween20,
0.02% $NaN_3$,
1% BSA Next, culture supernatant suitably diluted with Diluent Buffer was added to the wells at 100 μL/well, and allowed to react at room temperature for 1 hour. After washing with Rinse Buffer, alkaline phosphatase-conjugated goat anti-human IgM (BIOSOURCE) diluted 4,000 times with Diluent Buffer was added at 100 μL/well, and reacted at room temperature for 1 hour. Finally, wells were washed with Rinse Buffer, and alkaline phosphatase substrate (SIGMA) was added thereto. The absorbance was determined at the 405 nm measurement wavelength and 655 nm reference wavelength using Benchmark Plus absorption spectrometer (BioRad). The concentration of IgM was calculated by comparing with a purified anti-ganglioside GM3 human antibody (Hoon et al., Cancer Research 1993; 53: 5244-5250).

Each type of stable cell line expressing anti-ganglioside GM3 human antibodies was cultured in a 75 $cm^2$-culture flask at an initial cell density of 2×$10^5$ cells/mL. The IgM concentration in the culture supernatants was measured by the method described above. The results are shown in Table 2. The amount of IgM produced was approximately 20 mg/L on the third day and approximately 50 mg/L on the seventh day. The productivity indicating the production ability of a single cell was 5 to 19 pg/cell/day. Since IgM is a type of immunoglobulin that forms multimers, expression level of IgM in recombinants is low, and therefore, its large-scale preparation was considered difficult. However, the present results showed that highly productive recombinant IgM-expressing cells can be produced from CHO cells.

TABLE 2

| J-chain expression | Cell lines | Production amount after culturing for 3 days (mg/L) | Production amount after culturing for 7 days (mg/L) | Productivity (pg/cell/day) |
|---|---|---|---|---|
| Absent | CA02 | 24.1 | 36.9 | 14.1 |
| | CA15 | 11.8 | 39.7 | 4.9 |
| | CA19 | 27.1 | 62.3 | 13.1 |
| | CA20 | 20.2 | 35.4 | 10.5 |
| | CA24 | 25.0 | 41.5 | 10.7 |
| Present | CJ15 | 29.4 | N.T. | 19.4 |
| | CJ25 | 24.4 | N.T. | 18.1 |
| | CJ38 | 14.9 | N.T. | 12.4 |
| | CJ45 | 26.4 | N.T. | 18.7 |
| | CJ67 | 18.0 | N.T. | 12.8 |

N.T.: Not Tested

INDUSTRIAL APPLICABILITY

The present invention enabled stabilization of highly concentrated proteins in solutions at low temperature. Since the present invention enables stable long-term storage at low temperature of pharmaceutical formulations comprising proteins such as IgM as an active ingredient, it can significantly contribute to particularly the preparation of protein formulations.

The invention claimed is:

1. A method for suppressing cryoprecipitation of IgM in a solution at a temperature of 1° C. to 7° C., wherein the method comprises adding a citric acid buffer to a first solution comprising the IgM to form a second solution comprising the IgM at a concentration of 20 mg/ml or greater, and maintaining the second solution at 1° C. to 7° C., thereby suppressing cryoprecipitation of the IgM.

2. The method of claim 1, wherein the pH of the second solution is 5 to 8.

3. The method of claim 2, wherein the pH of the second solution is 5 to 6.

4. The method of claim 1, comprising cooling the second solution to a temperature of 7° C.

5. The method of claim 1, comprising cooling the second solution to a temperature of 4° C.

6. The method of claim 1, comprising cooling the second solution to a temperature of 1° C.

7. The method of claim 1, wherein the concentration of citric acid buffer in the second solution is 1 mM to 500 mM.

8. The method of claim 7, wherein the concentration of citric acid buffer in the second solution is 5 mM to 100 mM.

9. The method of claim 8, wherein the concentration of citric acid buffer in the second solution is 10 mM to 50 mM.

10. The method of claim 1, wherein the IgM is purified.

11. The method of claim 1, comprising cooling the second solution to a temperature between 1° C. and 7° C.

12. The method of claim 1, wherein the second solution is maintained at a temperature of 1° C.

13. The method of claim 1, wherein the second solution is maintained at a temperature of 4° C.

14. The method of claim 1, wherein the second solution is maintained at a temperature of 7° C.

15. The method of claim 1, wherein the concentration of the IgM in the second solution is 25 mg/ml or greater.

16. The method of claim 1, wherein cryoprecipitation of IgM is suppressed 30% or more, expressed as a cryoprecipitation increase suppression rate.

17. The method of claim 1, wherein cryoprecipitation of IgM is suppressed 50% or more, expressed as a cryoprecipitation increase suppression rate.

18. The method of claim 1, wherein cryoprecipitation of IgM is suppressed 80% or more, expressed as a cryoprecipitation increase suppression rate.

* * * * *